(12) United States Patent
Abe

(10) Patent No.: US 7,615,006 B2
(45) Date of Patent: Nov. 10, 2009

(54) ELECTRONIC ENDOSCOPE BATTERY SECTION

(75) Inventor: Kazunori Abe, Saitama (JP)

(73) Assignee: Fujinon Corporation, Saitama-shi, Saitama (JP)

( * ) Notice: Subject to any disclaimer, the term of this patent is extended or adjusted under 35 U.S.C. 154(b) by 498 days.

(21) Appl. No.: 11/390,140

(22) Filed: Mar. 28, 2006

(65) Prior Publication Data

US 2006/0220613 A1   Oct. 5, 2006

(30) Foreign Application Priority Data

Mar. 29, 2005   (JP)   ............... 2005-095275

(51) Int. Cl.
*A61B 1/00* (2006.01)
(52) U.S. Cl. .................................... 600/118
(58) Field of Classification Search ............... 600/178, 600/118, 117
See application file for complete search history.

(56) References Cited

U.S. PATENT DOCUMENTS

| 5,600,230 | A | * | 2/1997 | Dunstan ............... 340/636.13 |
| 5,608,306 | A | * | 3/1997 | Rybeck et al. ............. 320/106 |
| 5,965,997 | A | * | 10/1999 | Alwardi et al. ............. 320/132 |
| 6,078,871 | A | * | 6/2000 | Anderson .................... 702/63 |
| 6,174,617 | B1 | * | 1/2001 | Hiratsuka et al. ............ 429/90 |
| 6,202,642 | B1 | * | 3/2001 | McKinnon et al. ...... 128/200.23 |
| 6,294,894 | B1 | * | 9/2001 | Ochiai et al. ................ 320/132 |
| 6,494,827 | B1 | * | 12/2002 | Matsumoto et al. ......... 600/118 |
| 6,909,248 | B2 | * | 6/2005 | Clark ......................... 315/291 |
| 6,939,294 | B2 | * | 9/2005 | Abe ........................... 600/131 |
| 7,048,686 | B2 | * | 5/2006 | Kameya et al. ............ 600/179 |
| 2005/0049458 | A1 | * | 3/2005 | Honda et al. ................ 600/118 |
| 2005/0283047 | A1 | * | 12/2005 | Tashiro et al. ............... 600/118 |

FOREIGN PATENT DOCUMENTS

| JP | 2001-166222 A | 6/2001 |
| JP | 2003-275162 A | 9/2003 |
| JP | 2003-275174 A | 9/2003 |

* cited by examiner

*Primary Examiner*—John P Leubecker
(74) *Attorney, Agent, or Firm*—Birch, Stewart, Kolasch & Birch, LLP

(57) ABSTRACT

A battery section of an electronic endoscope is provided with an EEPROM. The EEPROM stores charging time and the number of charging of batteries, necessary for calculating remaining power of the batteries, and customized information for assigning functions to first, second and third switches of an operation section. A remaining-power calculator calculates the remaining power of the batteries based on a relation between discharge voltage and discharge time of the batteries as well as on the charging time and the number of charging of the batteries read out from the EEPROM. A function assignment circuit assigns the functions to the first, second and third switches in accordance with the customized information read out from the EEPROM.

4 Claims, 6 Drawing Sheets

ELECTRONIC ENDOSCOPE BATTERY SECTION

BACKGROUND OF THE INVENTION

1. Field of the Invention

The present invention relates to an electronic endoscope having a battery that supplies electric power.

2. Description of the Related Arts

Medical diagnoses using an electronic endoscope are widely performed. The electronic endoscope has a built-in imaging device such as a CCD at a front end of an insertion section, which is inserted into a body cavity. A processor device applies signal processing to the imaging signals obtained with the CCD, and the image inside of the body cavity (endoscopic image) can be observed on a monitor.

As one type of the electronic endoscopes, there is a so-called battery-powered electronic endoscope having a battery that supplies electric power (see Japanese Patent Laid-Open Publication No.2001-166222). The battery-powered electronic endoscope described in the above publication is provided with a charging circuit for changing the battery, a counter for counting the number of charging of the battery, and a voltage detector for detecting the remaining battery power. The counted number of charging and the detected remaining power are displayed by an LED provided on the battery or on an LCD panel.

The electronic endoscope is provided with various operation switches, such as a freeze switch for directing photographing/recording of a still image and a VCR switch for directing recording of the endoscopic image with a VCR. In actual endoscopic diagnoses, an operator observes the endoscopic image displayed on the monitor while operating these operation switches with one hand.

It is often the case that a plurality of electronic endoscopes are placed in a treatment room of the hospitals and used by different operators for different purposes depending on which region inside the body cavity is inspected or which operator uses the endoscope. Therefore, when the operation switch is fixed to one function as usual, it is sometimes inconvenient depending on the region to be inspected or the operator.

In order to solve the above problem, an electronic endoscope provided with a plurality of interchangeable operation switches, which can fit to any of a plurality of attachment portions, is proposed (see Japanese Patent Laid-Open Publication No.2003-275162). In addition, an electronic endoscope provided with a rotary switch for setting/changing the function of the operation switch as intended is proposed (see Japanese Patent Laid-Open Publication No.2003-275174).

In the Japanese Patent Laid-Open Publication No.2001-166222, however, it is assumed that the electronic endoscope uses one battery. Therefore, the electronic endoscope cannot accurately detect the remaining battery power when used with several batteries exchanged thereon.

In the electronic endoscope disclosed in the Japanese Patent Laid-Open Publication No.2003-275162, it is troublesome to remove and change the operation switches, and there is a risk that the operation switch may be lost when removed from the attachment portion. In the electronic endoscope disclosed in the Japanese Patent Laid-Open Publication No.2003-275174, a space for providing the rotary switch is required, so there is a problem that the article becomes large in dimension. Additionally, the combination of the operation switch and the function capable of being set and changed is limited.

SUMMARY OF THE INVENTION

An object of the present invention is to provide an electronic endoscope that corresponds with actual use and has excellent usability.

In order to achieve the above object, an electronic endoscope of the present invention includes a battery section and a rewritable memory. The battery section has a battery that supplies electric power. The memory is provided in the battery section.

In a preferable embodiment of the present invention, the memory stores charging time and the number of charging of the battery, and customized information. In the customized information, functions of plural operating members are specified. In the preferable embodiment of the present invention, the electronic endoscope includes a function assignment device for assigning the functions to the plural operating members in accordance with the customized information.

It is more preferable that the electronic endoscope includes a remaining-power calculator for calculating remaining battery power. The remaining power of the battery is calculated based on at least a relation between discharge voltage and discharge time of the battery, and the charging time and the number of charging of the battery stored in the memory.

According to the present invention, the battery section has the memory rewritable of data. For this configuration, it is possible to store the charging time and the number of charging of the battery, and the customized information in which the functions to be assigned to the plural operating members are specified in the memory. Therefore, the electrical endoscope that corresponds with the actual use and has excellent usability can be provided.

BRIEF DESCRIPTION OF THE DRAWINGS

The above and other subjects and advantages of the present invention will become apparent from the following detailed description of the preferred embodiments when read in association with the accompanying drawings, which are given by way of illustration only and thus are not limiting the present invention. In the drawings, like reference numerals designate like or corresponding parts throughout the several views, and wherein.

DETAILED DESCRIPTION OF THE PREFERRED EMBODIMENTS

Figure 1:
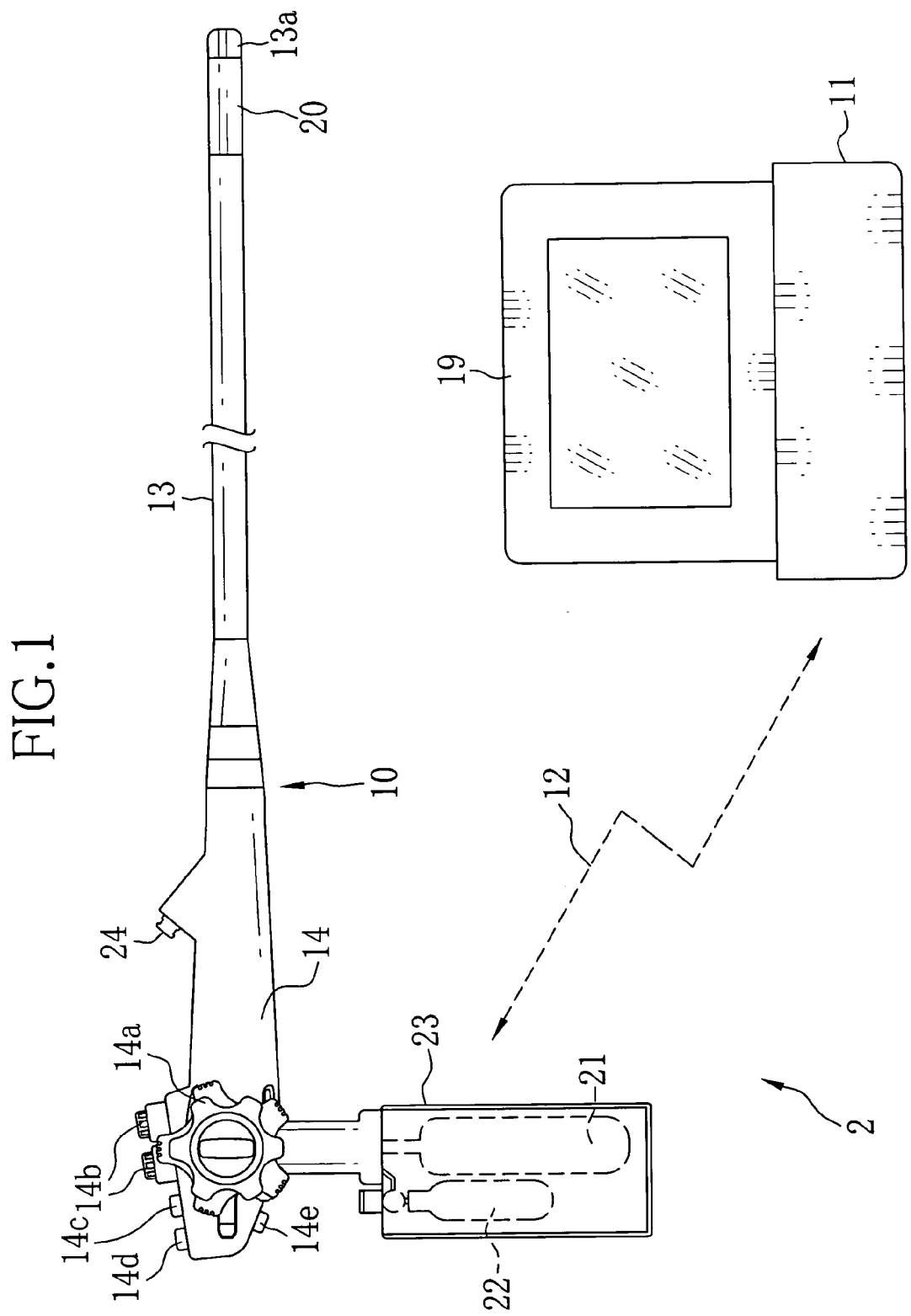
FIG. 1 is a schematic view showing composition of an electronic endoscope apparatus.

In FIG. 1, an electronic endoscope apparatus 2 is constituted of an electronic endoscope 10 and a processor device 11. The electronic endoscope 10 exchanges the signals with the processor device 11 by an electric wave 12.

The electronic endoscope 10 is provided with an insertion section 13 inserted into a body cavity and an operation section 14 connected to a base end portion of the insertion section 13. An objective lens 15, a CCD 16, an illumination lens 17 and an LED light source (hereinafter, LED) 18 (see FIG. 2) are built in a front end portion 13a provided at a front end of the insertion section 13. The objective lens 15 is for taking image light of a region to be inspected inside the body cavity. The CCD 16 is an imaging element for photographing images of the region to be inspected inside the body cavity. The LED 18 is for illuminating inside the body cavity. The image in the body cavity obtained by the CCD 16 is displayed as an endoscopic image on a monitor 19 connected to the processor device 11.

A curving portion 20 constituted of plural curving pieces jointed together is provided next to the front end portion 13a. A wire provided in the insertion section 13 is pushed and pulled by operating an angle knob 14a provided in the operation section 14 to curve and move the curving portion 20 from right to left and up and down so that the front end portion 13a can be directed in any direction inside the body cavity.

A cartridge 23 including a water tank 21 for storing water and an air bottle 22 for storing air is removably attached below the operation section 14. The water and air stored in the water tank 21 and the air bottle 22 respectively pass through each feed pipe provided in the electronic endoscope 10 in response to the operation of water/air feeding buttons 14b of the operation section 14, and are sprayed out of a cleaning nozzle (not shown) formed in the front end portion 13a toward the objective lens 15. Thereby, foreign matters adhered to a surface of the objective lens 15 is removed and the air is sent inside the body cavity. The cartridge 23 is positioned to be in contact with a wrist of the operator using the electronic endoscope 10 to stabilize the operability of the electronic endoscope 10. Note that reference numeral 24 represents a forceps opening through which a treatment tool is inserted.

The operation section 14 is provided with first, second and third switches 14c, 14d and 14e. The switches 14c to 14e are assigned with functions to work as a freeze switch for directing the photographing/recording of a still image, a VCR switch for directing the recording of the endoscopic image with a VCR, and the like. The function is assigned to each of the switches 14c to 14e by a function assignment circuit 50 (see FIG. 4).

Figure 2:
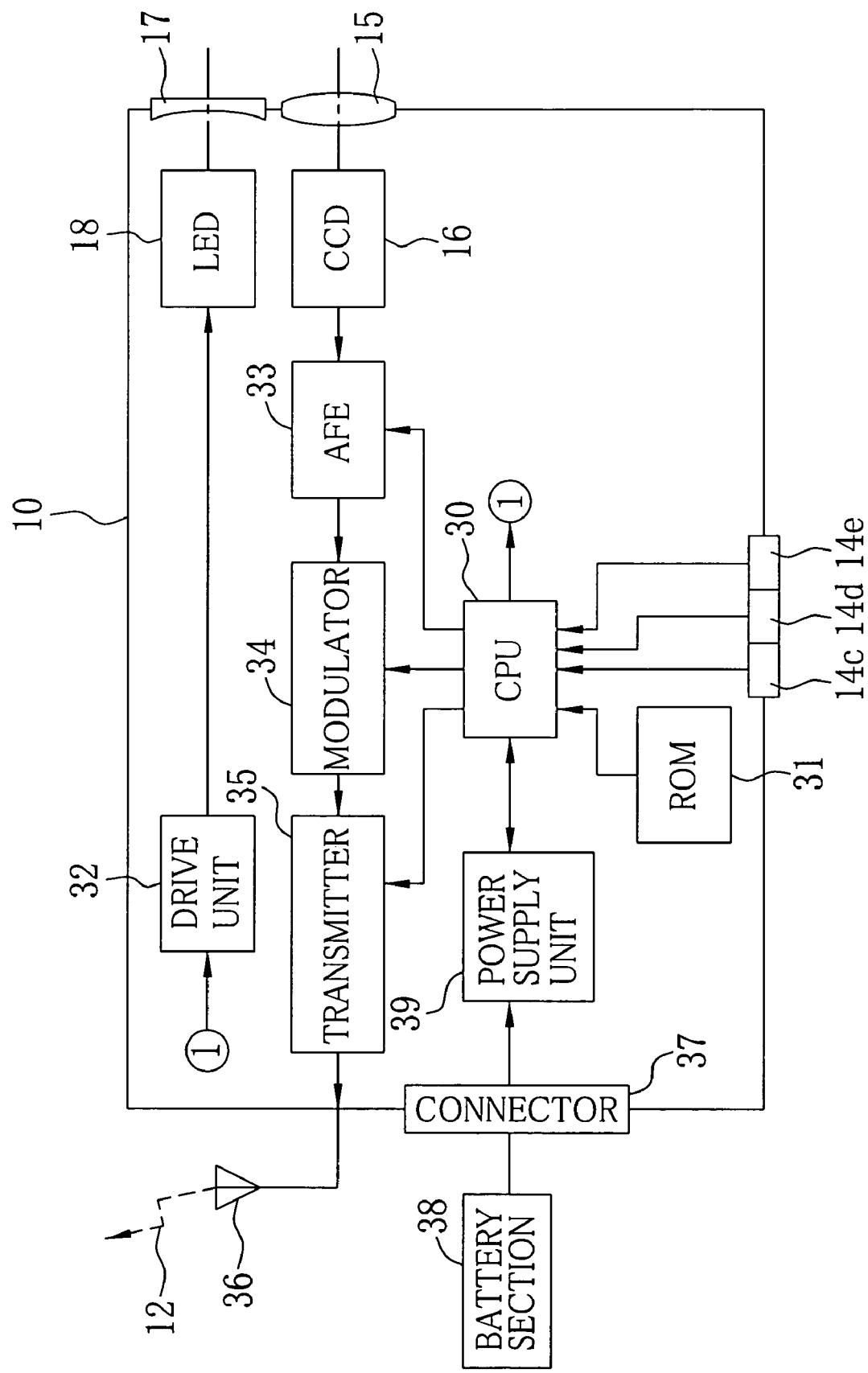
FIG. 2 is a block diagram showing an electrical structure of an electronic endoscope.

In FIG. 2, a CPU 30 controls the overall operation of the electronic endoscope 10. The switches 14c to 14e and a ROM 31 storing various programs and data for controlling the operation of the electronic endoscope 10 are connected with the CPU 30. The CPU 30 reads out the necessary program and data from the ROM 31 and controls the operation of the electronic endoscope 10. The CPU 30 also gets each part of the electronic endoscope 10 to operate in response to an operation signal from the first to third switches 14c to 14e.

A drive unit 32 is connected to the LED 18 and turns on/off the LED 18 under the control of the CPU 30. The light from the LED 18 illuminates the region to be inspected inside the body cavity through the illumination lens 17. The LED 18 may be provided in the operation section 14 and the light is directed to the front end portion 13a by a light guide.

The image light of the region to be inspected inside the body cavity is focused by the objective lens 15 on an imaging surface of the CCD 16, which outputs an imaging signal corresponding to the image light on each pixel. An AFE 33 applies correlation double sampling, amplification and A/D conversion to the imaging signal from the CCD 16 to convert it into a digital image signal.

A modulator 34 applies, for example, digital orthogonal modulation to the digital image signal output from the AFE 33 to generate an RF signal. A transmitter 35 transmits the RF signal as the electric wave 12 having a first or second frequency band (e.g. 1.2 GHz or 2.4 GHz) to the processor device 11.

A battery section 38 is connected to a connector 37. The battery section 38 has batteries 38a incorporated therein. The batteries 38a are, for example, two nickel-hydrogen batteries of a rated voltage 1.2V electrically connected in series. The electric power of the batteries 38a is supplied to each section of the electronic endoscope 10 through a power supply unit 39 controlled by the CPU 30. A chamber (not shown) for containing the battery section 38 is provided at the rear end of the operation section 14, and the connector 37 is arranged inside the chamber.

Figure 3:
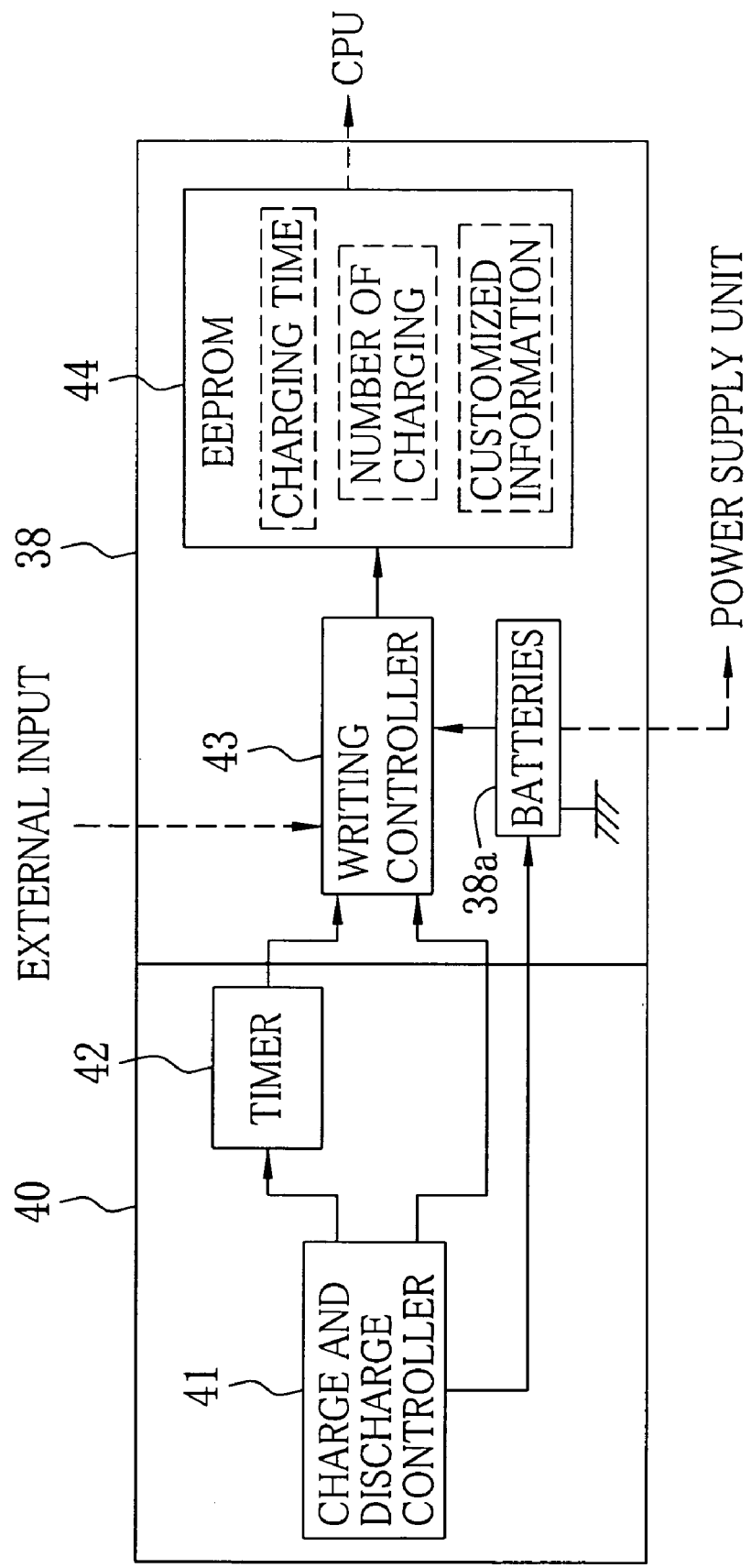
FIG. 3 is a block diagram showing an electrical structure of a battery section.

In FIG. 3, a battery charger 40 for charging the batteries 38a is provided with a charge and discharge controller 41 and a timer 42. The battery section 38 is provided with a writing controller 43 and an EEPROM 44. When the battery section 38 is connected to the battery charger 40, the charge and discharge controller 41 discharges the residual electric power in the batteries 38a, before starting the charging of the batteries 38a in order to prevent a memory effect. The charge and discharge controller 41 then charges the electric power in the batteries 38a. Note that the battery charger 40 may be integrated with the battery section 38, or may be separated from the battery section 38.

When the batteries 38a reach a full charge, the charge and discharge controller 41 sends a signal, which indicates the full charging, to the writing controller 43. In response to the signal from the charge and discharge controller 41, the writing controller 43 increments the number of charging of the batteries 38a stored in the EEPROM 44 by "1". When the charging is stopped due to, for example, a blackout during charging of the batteries 38a, the charge and discharge controller 41 does not send the signal indicating the full charging. Owing to this, the number of charging of the batteries 38a stored in the EEPROM 44 does not change at this time.

The timer 42 measures the time taken by the charge and discharge circuit 41 to charge the batteries 38a, and sends the measurement result to the writing controller 43. The writing controller 43 writes the measurement result from the timer 42, that is, the charging time of the batteries 38a, in the EEPROM 44.

The writing controller 43 writes customized information, input from an external apparatus such as a ROM writer, in the EEPROM 44. In the customized information, the functions of the first to third switches 14c to 14e are specified. The content of the customized information varies from operator to operator. The customized information is referred to when the function assignment circuit 50 assigns the functions.

Figure 4:
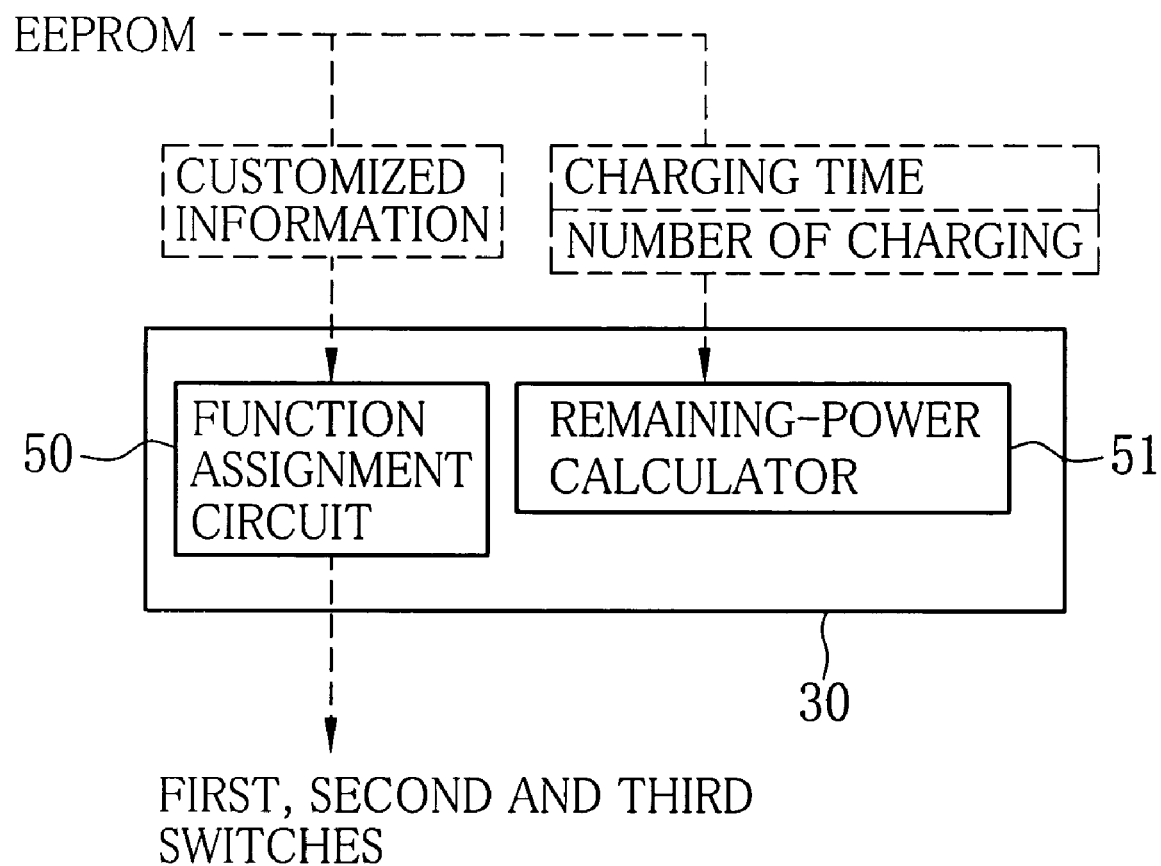
FIG. 4 is a block diagram showing an electrical structure of a CPU of the electronic endoscope.

In FIG. 4, the CPU 30 is provided with the function assignment circuit 50 and a remaining-power calculator 51. The function assignment circuit 50 is constituted of, for example, plural switching elements for changing an input path of the operation signal from the first to third switches 14c to 14e to the CPU 30. The function assignment circuit 50 assigns the functions to the first to third switches 14c to 14e in accordance with the customized information from the EEPROM 44.

Figure 5:
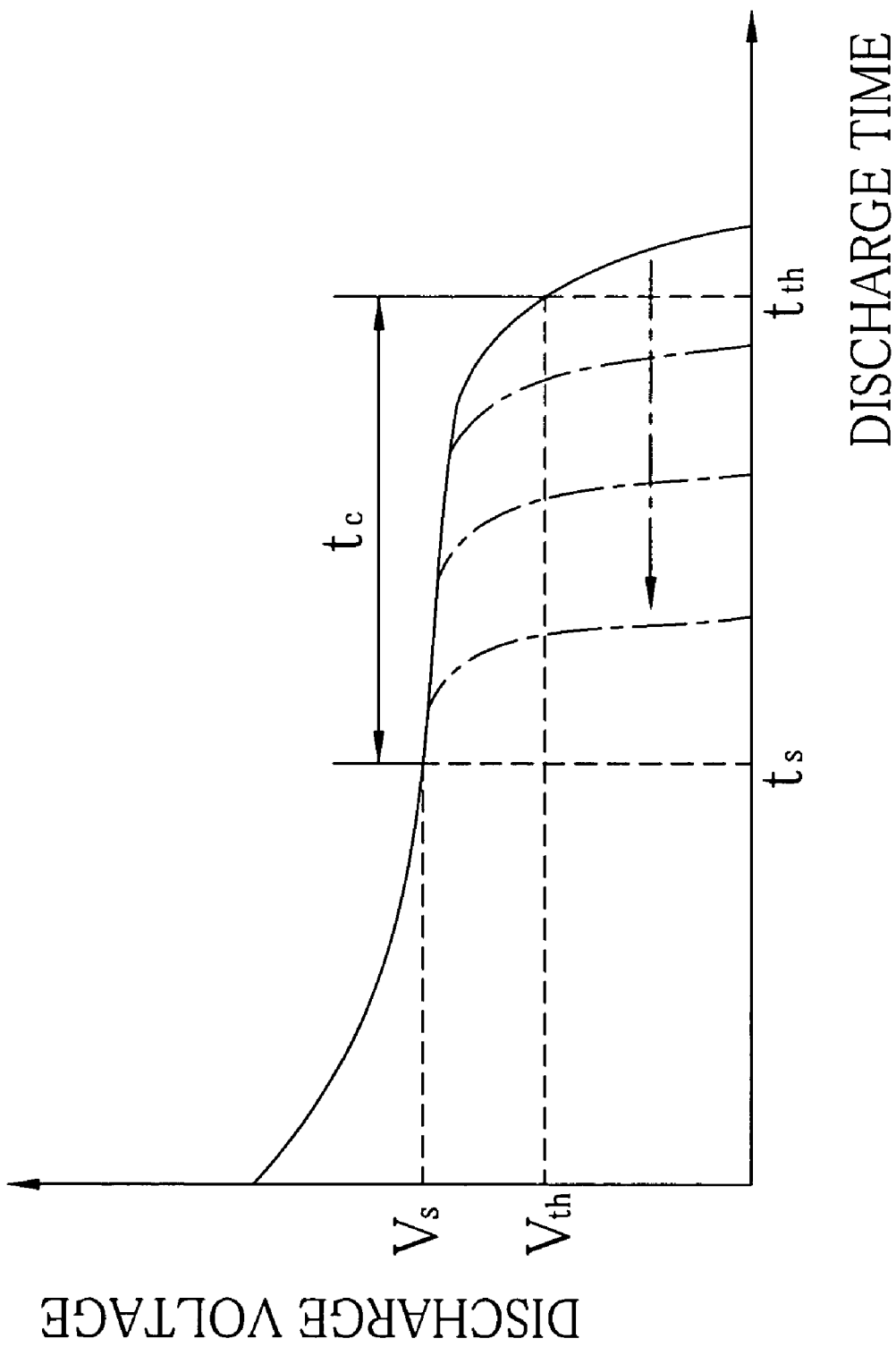
FIG. 5 is a graph showing a relation between discharge voltage and discharge time of batteries.

The remaining-power calculator 51 calculates the remaining power of the batteries 38a based on a relation between the discharge voltage and discharge time of the batteries 38a shown in FIG. 5, and the charging time and the number of charging of the batteries 38a from the EEPROM 44. It can be seen from the relation between the discharge voltage and discharge time of the batteries 38a in FIG. 5 that the discharge voltage gradually decreases as time passes after the initiation of the usage of the batteries 38a, and it rapidly falls at a certain point in time. As shown by the chain line arrow in FIG. 5, the discharge voltage decreases faster as the number of charging increases.

In order to calculate the remaining power of the batteries 38a by the remaining-power calculator 51, for instance, the relation between the discharge voltage and discharge time of the batteries 38a as shown in FIG. 5 is preliminarily stored as a data table or arithmetic expression in the ROM 31. The discharge voltage at the usage limit of the batteries 38a is defined as $V_{th}$, and the discharge time at this limit is defined as $t_{th}$. $t_{th}$ is the power duration of the batteries 38a per one full charge. $V_{th}$ and $t_{th}$ are preliminarily set, and $t_{th}$ becomes shorter as the number of charging increases. $V_{th}$ and $t_{th}$ are practically set close to the limit with a small margin. The voltage at the initiation of the usage of the batteries 38a is defined as $V_s$. and the discharge time at this time is defined as $t_s$. $V_s$ and $T_s$. are obtained from the charging time from the EEPROM 44, whereas $t_{th}$ is obtained from the number of charging from the EEPROM 44. After that $t_c$ as the available time of the batteries 38a (hereinafter available time $t_c$) is calculated from the following equation: $t_{th} - t_s$.

Next, $t_{timer}$ as photographing time of the endoscopic image is measured by a timer (not shown), and the remaining power of the batteries 38a is obtained by subtracting $t_{timer}$ from the calculated available time $t_c$. The remaining power of the batteries 38a is displayed, for example, by the LED 18 provided adjacent to the operation section 14 or on a remaining power display (not shown) constituted of a LCD monitor and so forth. Note that the number of charging of the batteries 38a may be displayed. It is also possible to constantly measure the discharge voltage of the batteries 38a and calculate the remaining power of the batteries 38a in conjunction with this measurement result.

Figure 6:
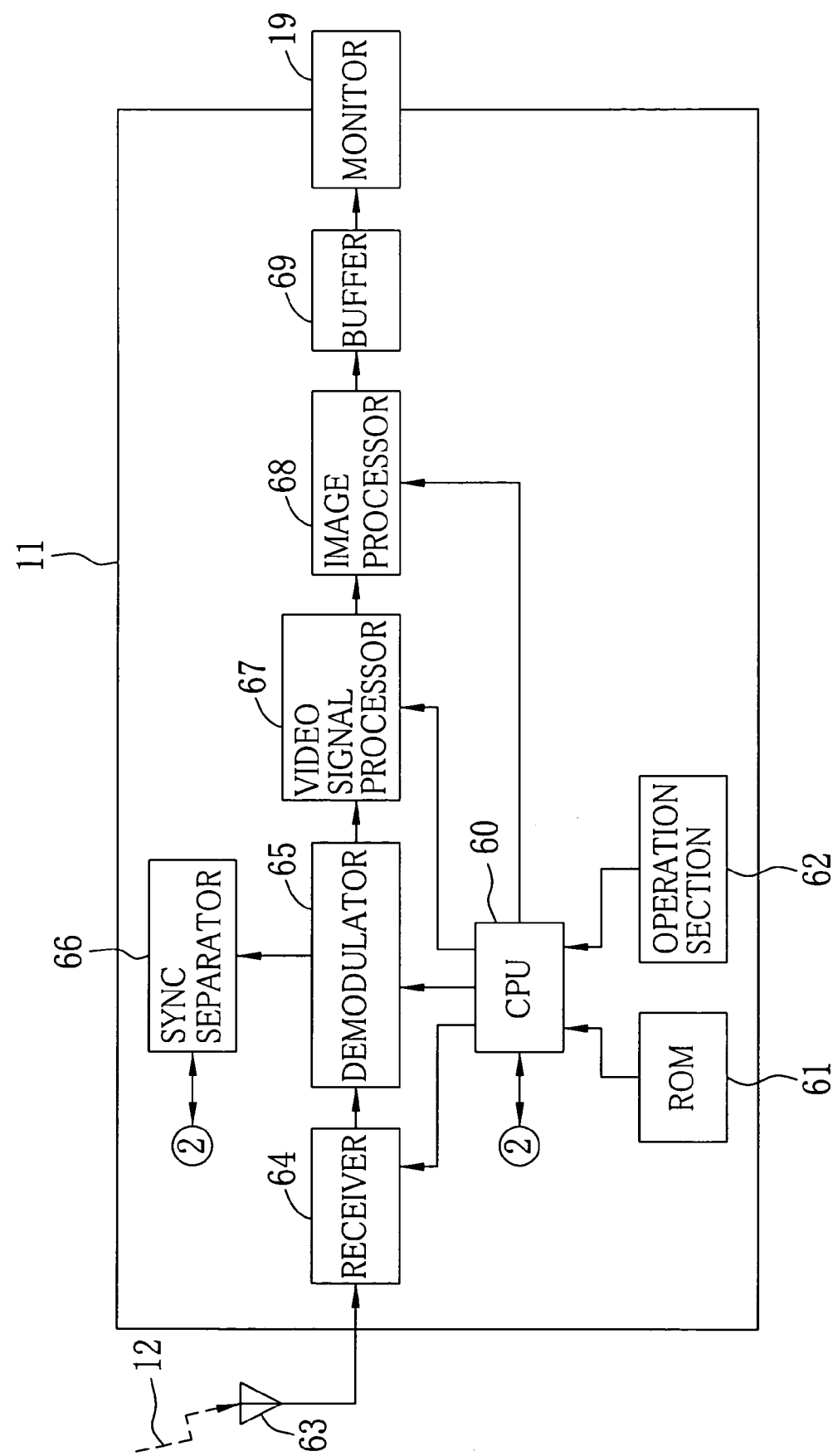
FIG. 6 is a block diagram showing an electrical structure of a processor device.

In FIG. 6, a CPU 60 controls the overall operation of the processor device 11. A ROM 61 storing various programs and data for controlling the operation of the processor device 11 and an operation section 62 constituted of a key board and mouse are connected to the CPU 60. The CPU 60 reads out the necessary program and data from the ROM 61 and controls the operation of the processor device 11. The CPU 60 also activates each part of the processor device 11 in response to an operation signal from the operation section 62.

An antenna 63 receives the electric wave 12 from the electronic endoscope 10. A receiver 64 amplifies the electric wave 12, that is, the RF signal, received by the antenna 63. A demodulator 65 applies, for example, the digital orthogonal detection to the RF signal to demodulate it into the image signal before being modulated in the electronic endoscope 10.

A sync separator 66 separates a synchronizing signal from the image signal demodulated in the demodulator 65 by amplitude separation, and then separates a horizontal synchronizing signal and a vertical synchronizing signal by frequency separation. A video signal processor 67 produces a digital video signal from the image signal. An image processor 68 applies various kinds of image processing such as masking and character information addition to the video signal produced in the video signal processor 67. A buffer 69 temporarily stores the video signal to which the various kinds of processing are applied to be displayed as the endoscopic image on the monitor 19.

When the electronic endoscope apparatus 2 having the above-mentioned structure is used to observe the inside of the body cavity, the insertion section 13 is inserted into the body cavity, and then the image is obtained by the CCD 16 while the LED 18 illuminates the inside of the body cavity to provide the endoscopic image on the monitor 19.

At this time, the image light of the region to be inspected inside the body cavity is focused by the objective lens 15 on the imaging surface of the CCD 16, and the image signal is output from the CCD 16. The AFE 33 applies the correlation double sampling, amplification and A/D conversion to the image signal to convert it into the digital image signal.

The modulator 34 applies the digital orthogonal modulation to the digital image signal output from the AFE 33 to generate the RF signal. The RF signal is amplified in the transmitter 35 to be transmitted as the electric wave 12 from the antenna 36.

In the processor device 11, when the electric wave 12 from the antenna 36 is received by the antenna 63, the electric wave 12, that is, the RF signal, is amplified in the receiver 64. The demodulator 65 applies the digital orthogonal detection to the amplified RF signal to demodulate it into the image signal before being modulated in the electronic endoscope 10.

The sync separator 66 applies the synchronizing separation to the image signal demodulated in the demodulator 65 under the control of the CPU 60, and the image signal as the digital video signal is output from the video signal processor 67. The video signal to which the various kinds of image processing are applied in the image processor 68 is temporarily stored in the buffer 69 and displayed as the endoscopic image on the monitor 19. As mentioned above, the data of the endoscopic image is sent and received between the electronic endoscope 10 and the processor device 11 by the electric wave 12.

The charging time of the batteries 38a measured by the timer 42 of the battery charger 40, the number of charging of the batteries 38a incremented in response to the signal indicating the full charging from the charge and discharge controller 41, and the customized information are written in the EEPROM 44 of the battery section 38 by the writing controller 43. The charging time and the number of charging of the batteries 38a, and the customized information written in the EEPROM 44 are sent to the CPU 30 through the connector 37 when the power of the electronic endoscope 10 in which the battery section 38 is loaded is turned on.

The function assignment circuit 50 of the CPU 30 assigns the functions to the first, second and third switches 14c, 14d and 14e of the operation section 14 in accordance with the customized information from the EEPROM 44. The remaining-power calculator 51 calculates the remaining power of the batteries 38a based on the relation between the discharge voltage and the discharge time of the batteries 38a, and the charging time and the number of charging of the batteries 38a input from the EEPROM 44. The calculated remaining power is displayed on the remaining power display.

As mentioned above, in the electronic endoscope 10 of the present invention, the EEPROM 44 is built in the battery section 38 and stores the charging time and the number of charging required for calculating the remaining power of the batteries 38a. For this configuration, the electronic endoscope 10 can accurately calculate the remaining power of the batteries 38a when used with several battery sections 38 exchanged thereon.

Moreover, the customized information for assigning the functions to the first, second and third switches 14c, 14d and 14e of the operation section 14 is stored in the EEPROM 44. For this configuration, the function can be set different for each operator. In addition, when each operator has own battery section 38 storing customized information set according to one's preference or to the region to be inspected inside the body cavity, the operators can operate the electronic endoscope 10 with excellent usability in accordance with their preference or the region to be inspected only by loading their own battery section 38 to the electronic endoscope 10.

In addition to the charging time and the number of charging of the batteries 38*a*, and the customized information, for example, name and department of the operator may be stored in the EEPROM 44.

In the above embodiment, the writing controller 43 is provided in the battery section 38, but it may be provided in the battery charger 40.

In the above embodiment, the electronic endoscope apparatus 2 that exchanges signals by the electric wave 12 is explained as the example. However, the present invention is not limited to this, and it is applicable to the conventional electronic endoscope apparatuses in which the electronic endoscope and the processor device are connected to each other through a signal cable, as long as the electronic endoscope is the battery-powered type.

In the above embodiment, the electronic endoscope apparatus 2 is explained as it is for medical use, however the present invention is not limited to this. The electronic endoscope apparatus 2 is applicable to other industrial use, such as for photographing images in narrow pipes and the like.

Although the present invention has been fully described by the way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic endoscope for photographing an image of a region to be inspected of a subject, said electronic endoscope comprising:
    a battery section including a battery for supplying electric power; and
    a rewritable memory provided in said battery section, the rewritable memory including a charging time section,
    the battery section further including
        a charge controller that charges the battery,
        a timer connected to the charge controller that measures a time for charging the battery, and
        a writing controller connected to both the timer and the charge controller, wherein
            the writing controller writes the measured time for charging the battery from the timer to the charging time section of the rewritable memory,
    wherein said rewritable memory additionally stores a relation between a discharge voltage and discharge time of the battery as a data table or as an arithmetic expression, the electronic endoscope further comprising:
    a remaining-power calculator for calculating remaining power of said battery based on at least the relation between discharge voltage and discharge time of said battery, and said charging time and the number of times of charging the battery stored in said rewritable memory.

2. The electronic endoscope as claimed in claim 1, wherein said rewritable memory further includes a number of times of charging the battery section.

3. The electronic endoscope as claimed in claim 2, wherein every time the charge controller charges the battery, the writing controller increments the number of times of charging the battery section of the rewritable memory by one.

4. An electronic endoscope for photographing an image of a region to be inspected of a subject, said electronic endoscope comprising:
    a battery section including a battery for supplying electric power; and
    a plurality of switches, each switch performing a certain function when activated;
    the battery section further including:
        a rewritable memory, said rewritable memory having a customized information Section, and
        a writing controller for writing customized information relating to said certain function to be assigned to each of said plurality of switches,
    the electronic endoscope further comprising:
    a function assignment device for assigning said certain function to each of said plurality of switches in accordance with said customized information, said certain function relating to an operation of said electronic endoscope.

* * * * *